United States Patent [19]
Igaue et al.

[11] Patent Number: 5,858,151
[45] Date of Patent: Jan. 12, 1999

[54] PROCESS FOR MANUFACTURING A SHEET MEMBER FORMING A PART OF DISPOSABLE GARMENT

[75] Inventors: Takamitsu Igaue; Toshifumi Otsubo; Toru Sasaki, all of Ehime-ken, Japan

[73] Assignee: Uni-Charm Corporation, Ehime-ken, Japan

[21] Appl. No.: 804,553

[22] Filed: Feb. 24, 1997

[30] Foreign Application Priority Data

Feb. 28, 1996 [JP] Japan .................................. 8-041383

[51] Int. Cl.⁶ ...................................................... A61F 13/15
[52] U.S. Cl. .......................... 156/164; 156/163; 156/229; 156/264; 156/265; 604/385.1; 604/385.2
[58] Field of Search ..................................... 156/163, 164, 156/229, 264, 265; 604/385.1, 385.2

[56] References Cited

U.S. PATENT DOCUMENTS

| | | | |
|---|---|---|---|
| 4,595,441 | 6/1986 | Holvoet et al. | ........................ 156/265 |
| 5,110,386 | 5/1992 | Ochi et al. | ........................ 156/265 X |
| 5,147,487 | 9/1992 | Nomura et al. | . |
| 5,330,598 | 7/1994 | Erdman et al. | ........................ 156/164 |
| 5,439,459 | 8/1995 | Tanji et al. | ........................ 156/265 X |

Primary Examiner—Jeff H. Aftergut
Attorney, Agent, or Firm—Lowe, Price, LeBlanc & Becker

[57] ABSTRACT

A web intended to be used as a topsheet or a backsheet defining front and rear sections and a crotch section extending therebetween in a disposable garment is continuously fed in its longitudinal direction, and a width of the web is divided in two halves along a longitudinally extending cutting line describing a curve approximate to a sine curve in and thus two webs are obtained. These two webs are transversely spaced from each other by a predetermined dimension and one of these two webs is longitudinally shifted relatively to the other by ½ period. Thereafter, these two webs are joined together in their overlapping regions. The two webs thus joined together is cut for every period with each pair of such overlapping regions lying in a middle of this period. The invention can thereby provide the topsheet or the backsheet without any waste pieces cut therefrom.

2 Claims, 3 Drawing Sheets

PROCESS FOR MANUFACTURING A SHEET MEMBER FORMING A PART OF DISPOSABLE GARMENT

BACKGROUND OF THE INVENTION

The present invention relates to a process for manufacturing a sheet member intended to be used as a topsheet or a backsheet forming a part of a disposable garment such as a disposable diaper, training pants, incontinence pants and the like.

There have been proposed various disposable garments such as disposable diapers, training pants and incontinence pants having a front section, a rear section and a crotch section extending therebetween. In general, such garment comprises a skin-contactable topsheet, a skin-noncontactable backsheet and optionally a liquid-absorbent core disposed therebetween. In these sheets, the crotch section has transversely opposite side edges thereof curved inward with respect to the garment to improve a fitness around the wearer's legs and the sheets as a whole present a sandglass-shape in unfolded states thereof.

The topsheet or backsheet in such sandglass-shape can be obtained by cutting off substantially semicircular pieces from transversely opposite long sides of a rectangular nonwoven fibrous sheet or plastic film. However, these semicircular pieces of sheets are usually discarded as waste pieces and material is correspondingly wasted.

SUMMARY OF THE INVENTION

In view of the problem as mentioned above, it is a principal object of the invention to provide a process for manufacturing a sheet member intended to be used as a topsheet or a backsheet forming a part of a disposable garment allowing transversely opposite side edges of a crotch section of the garment to be curved inward with respect to the garment and thereby to obtain a sandglass-shaped topsheet or backsheet without any wasteful use of material.

The object set forth above is achieved, according to the invention, by a process for manufacturing a sheet member intended to be used as a topsheet or a backsheet forming a part of front and rear sections of a disposable garment having the front section, the rear section and a crotch section of the garment extending between the front and rear sections, the crotch section having transversely opposite side edges curved inward with respect to the garment, the process for manufacturing the sheet member at least comprising the steps of:

a. continuously feeding a web intended to form the topsheet or the backsheet in a longitudinal direction thereof;

b. dividing a width of the web in two halves along a cutting line continuously extending in the longitudinal direction and describing a curve approximate to a sine curve defined by a predetermined period and amplitude;

c. shifting any one half of the divided web relatively to the other half in said longitudinal direction by odd times of ½ of said period;

d. transversely spacing the two halves of the web from each other by a dimension which is equal to or less than said amplitude;e. integrally joining the two halves of the web after the steps c and d in overlapping regions thereof; and f. cutting the two halves of the web along transversal cutting lines each provided for every period with each pair of the overlapping and joined regions lying in a middle of each said period.

The process according to the invention can be useful not only for manufacturing the backsheet as in the embodiment as described above but also for manufacturing the topsheet. These topsheet and backsheet may be not only those employed in the flat type disposable diaper as in the illustrated embodiment but also those employed in the other garments such as shorts-type disposable diaper, training pants and incontinent pants.

According to the inventive process for manufacturing topsheet or backsheet of garment, the web continuously fed is divided in two halves along the cutting line describing the longitudinally extending sine curve and one of the two halves of the web is shifted relatively to the other half longitudinally as well as transversely so as to form the curved edges intended to surround the wearer's legs, respectively. Accordingly, the process of the invention produces no waste pieces of a cut web.

Securing of the elastic members performed along the cutting line advantageously facilitates placement of the elastic members extending along the edges adopted to surround the wearer's legs and also extending across the crotch section simply by joining the front and rear sections to each other. Furthermore, the elastic members to be laid along front and rear halves of the edge around each leg-opening, respectively, can be secured to the web by oscillating these elastic members together in the same direction along the cutting line. In this way, means for placement of the elastic members can be correspondingly simplified in comparison with the conventional technique by which the elastic members must be oscillated in different directions.

Other objects, advantages and features of the invention will be apparent from the following description.

DESCRIPTION OF PREFERRED EMBODIMENT

Figure 1:
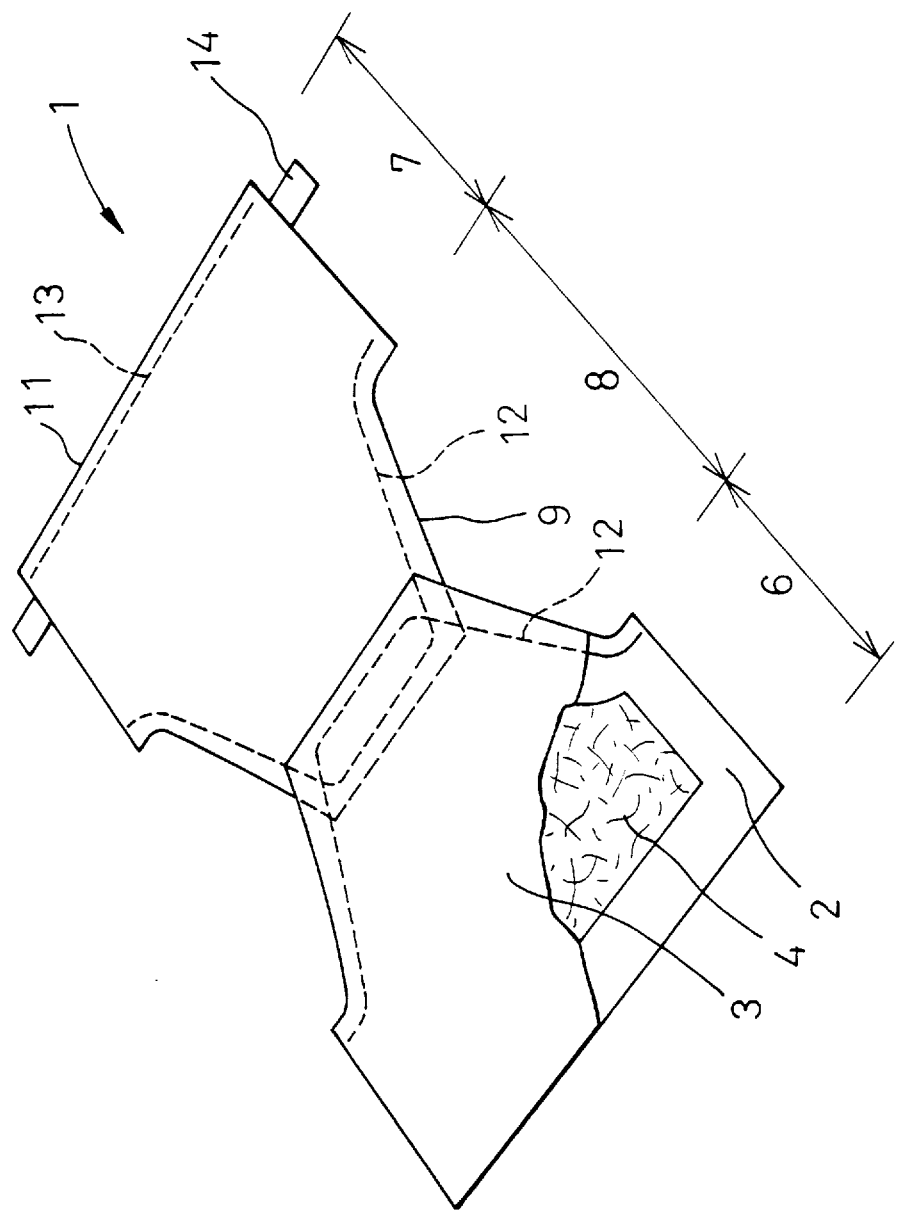
FIG. 1 is a perspective view of a diaper as partially broken away.

FIG. 1 is a perspective view showing a diaper 1 as viewed from its rear side and as partially broken away, in which the diaper 1 comprises a liquid-permeable topsheet 2 made of nonwoven fibrous sheet, a liquid-impermeable backsheet 3 made of plastic film and a liquid-absorbent core 4 disposed therebetween. The diaper 1 has a front section 6, a rear section 7 and a crotch section 8 extending therebetween. The topsheet 2 and the backsheet 3 are joined to each other along portions thereof extending outward beyond a peripheral edge of the core 4. Transversely opposite side edges of the crotch section 8 are curved inward with respect to the diaper 1 to define edges 9 of respective leg-openings. Along the respective leg-openings' edges 9 and along an upper end of the rear section there are provided elastic members 12, 13, respectively, so as to be disposed between the topsheet 2 and backsheet 3 and to be secured in a longitudinally extended state thereof to an inner surface of the topsheet 2 and/or the backsheet 3. The elastic member 12 associated with the leg-openings further extends across the crotch section 8, i.e., between the respective leg-openings' edges 9, as will be described later more in detail. A pair of tape fasteners 14 extend outward from transversely opposite side edges of the rear section 7.

Figure 2:
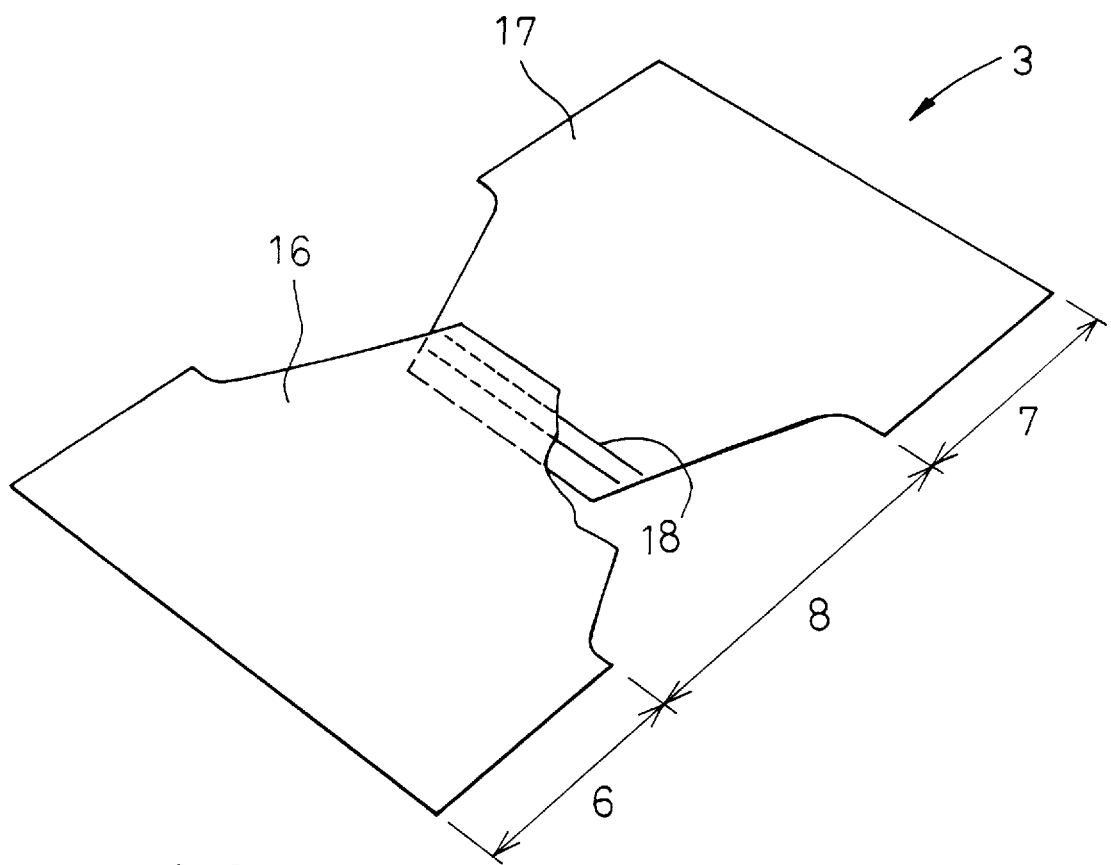
FIG. 2 is a perspective view of a backsheet as partially broken away.

The backsheet 3 shown by FIG. 2 in a perspective view as partially broken away comprises a front sheet 16 forming the front section 6 and approximately a front half of the crotch section 8 extending from the front section 6, on one hand, and a rear sheet 7 forming the rear section 7 and approximately a rear half of the crotch section 7, on the other hand. These two sheets 16, 17 overlap each other in a longitudinally middle region of the crotch section 8 and are integrally joined to each other along an adhesive line 18 continuously extending across the diaper 1 to assume a sandglass-like shape. The topsheet 2 is made of a single sheet of nonwoven fibrous sheet which is identical to the backsheet 3 with respect to a shape and size thereof, while the topsheet 2 is not illustrated in detail.

Figure 3A:
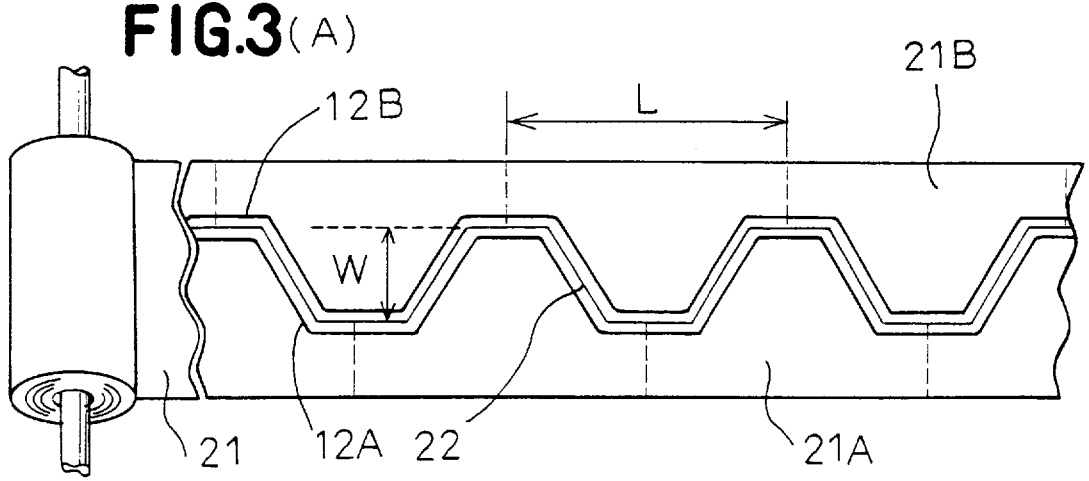
FIG. 3(A)–3(C) are schematic diagrams illustrating a process for manufacturing the backsheet, the process going through steps (A), (B) and (C).
Figure 3B:
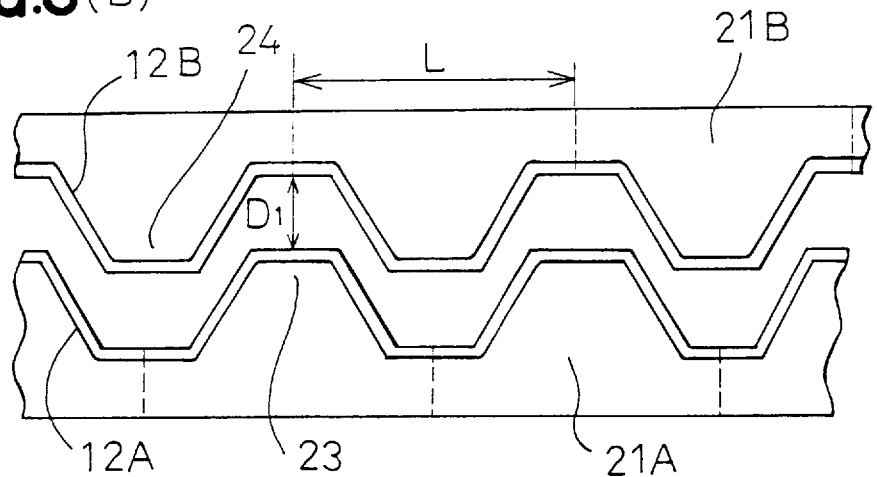
Figure 3C:
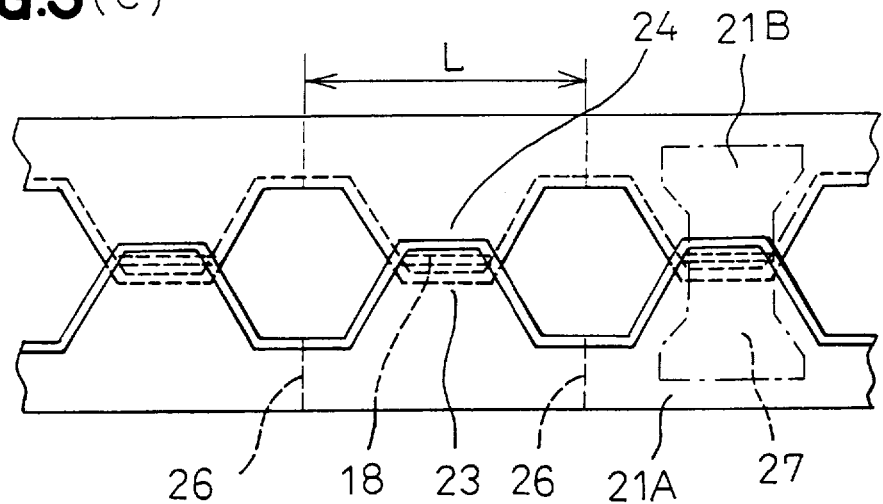

FIG. 3 is a schematic diagram illustrating a process for continuously manufacturing the backsheet 3, the process going through steps (A), (B) and (C). At the step (A), continuous uncut film 21 adapted to form the backsheet 3 is longitudinally fed from a source roll thereof. The uncut film 21 passes a cutter (not shown) adapted to oscillate at an amplitude W in a transverse direction thereof and a period L in a longitudinal direction thereof along a continuous cutting line 22 describing a curve approximate to a sine curve. The uncut film 21 is thus cut at a transversal middle thereof in two halves, i.e., film strips 21A and 21B which longitudinally extend, respectively. In this regard, it should be understood that, before the uncut film 21 is provided with the cutting line 22, continuous elastic members 12A, 12B may be secured in a longitudinally extended state thereof to the uncut film 21 so as to extend parallel to the predetermined cutting line 22 on either side thereof, as shown by FIG. 3, by using a traverse technique which is known from the disclosure of U.S. Pat. No. 5,147,487, issued to Nomura et al, which is herein incorporated by referenced and adapted to place the elastic members on the backsheet along the curve approximate to a sine curve. These elastic members 12A, 12B form together at the final step the previously mentioned elastic member 12 associated with the leg-openings.

At the step (B), the film strips 21A, 21B are transversely spaced from each other by a predetermined dimension $D_1$. The dimension $D_1$ is controlled to be equal to or less than the amplitude W.

At the step (C), one of the film strips 21A and 21B is longitudinally shifted relatively to the other by one half period L/2 or odd times thereof so that regions 23 of the film strip 21A in the proximity of respective crests of the cutting line 22 (Refer to the step B) may overlap regions 24 of the film strip 21B in the proximity of respective troughs of the cutting line 22. In these overlapping regions 23, 24, the film strips 21a and 21B are joined together by respective joining lines 18. To achieve such joining, one of these film strips 21A, 21B may be applied with hot melt adhesive to form the linear adhesive lines 18 or may be heat-sealed to each other. After these film strips 21A, 21B have been joined together, each pair of the regions 23, 24 associated with each other in which the film strips 21A, 21B have been joined together lies at a middle of each period L of the cutting line 22. The film strips 21A, 21B are successively cut along transversal cutting lines 26 (indicated by broken lines) each provided for every period L to obtain individual backsheets 3 one of which is shown by FIG. 2. In this regard, it should be understood that, at the step (C), a liquid-absorbent core 27 indicated by an imaginary line may be placed on the film strips 21A, 21b, then a web of nonwoven fibrous sheet adopted to form the topsheet 2 may be placed on the core 27 and the film strip 21A may be joined to the film strip 21B around the core 27 before the cutting lines 26 are formed.

In the individual backsheet 3 obtained through the steps (A), (B) and (C), oblique edges extending between the respective pairs of adjacent crests and troughs of the cutting line 22 describing the curve approximate to the sine curve define the curved edges 9 intended to surround the wearer's legs, respectively. The continuous elastic members 12A, 12B forming together the elastic member 12 associated with the respective leg-openings extend along the cutting line so that, in the individual backsheet 3, these elastic members 12A, 12B extend across the crotch section 8 as will be seen in FIG. 2 and also intersect each other in the proximity of transversely opposite side edges of the crotch section 8. Though not shown, the film strips 21A, 21B having the elastic members 12A, 12B secured thereto are held by appropriate means to prevent the film strips from being wrinkled due to contraction of these elastic members 12A, 12B and 13A.

Materials employed for the topsheet 2 and backsheet 3 of this invention are not limited to those employed by the above described embodiment in reference with the accompanying drawings. For example, it is also possible to employ porous plastic film as material for the topsheet 2 and to employ nonwoven fibrous sheet or laminate of nonwoven fibrous sheet and plastic film as material for the backsheet 3. Each of the elastic members 12A, 12B may comprise a plurality of elastic elements.

The entire disclosure of Japanese Patent Application No. Hei 8-41383 filed on Feb. 28, 1996 including specification, claims drawings and abstract are herein incorporated by reference in its entirety.

What is claimed is:

1. A process for manufacturing a sheet member intended to be used as a topsheet or a backsheet forming front and rear sections of a disposable garment comprising the front section, the rear section and a crotch section extending therebetween, the crotch section having transversely opposite side edges curved inward with respect to the garment, the process for manufacturing the sheet member at least comprising the steps of:

a. continuously feeding web intended to form the topsheet or backsheet in a longitudinal direction thereof;

b. dividing a width of the web in two halves along a cutting line continuously extending in said longitudinal direction and describing a curve approximate to a sine curve defined by a predetermined period and amplitude;

c. shifting any one half of the divided web relatively to the other half in said longitudinal direction by odd times of ½ of said period;

d. transversely spacing the two halves of the web from each other by a dimension which is equal to or less than said amplitude;

e. integrally joining the two halves of the divided web after the steps c and d in overlapping regions thereof; and f. cutting the two halves of the divided web along transversal cutting lines each provided for every period with each pair of the overlapping and joined regions lying in a middle of each period.

2. A process according to claim 1, wherein elastic members are secured in a longitudinally extended state thereof to the web parallel to said cutting line on either side thereof before the width of the web is cut in two halves along said cutting line.

* * * * *